United States Patent [19]
Rayl et al.

[11] 3,949,390
[45] Apr. 6, 1976

[54] HIGH VOLTAGE AEROSOL DETECTOR

[75] Inventors: Martin Rayl, Trenton; Harold Duane Hanson, East Brunswick, both of N.J.; Billy Wesley Beyers, Jr., Greenfield, Ind.

[73] Assignee: RCA Corporation, New York, N.Y.

[22] Filed: June 5, 1974

[21] Appl. No.: 476,445

[52] U.S. Cl............................ 340/237 S; 340/237 R
[51] Int. Cl.².............................................. G08B 17/10
[58] Field of Search......... 340/237, 227 R; 250/324, 250/325, 326; 324/33; 178/7.9

[56] References Cited
UNITED STATES PATENTS

| | | |
|---|---|---|
| 3,439,261 | 4/1969 | Loh et al. ............................ 324/33 |
| 3,460,125 | 8/1969 | Liebermann et al. ........ 340/237 R X |
| 3,728,615 | 4/1973 | Hill et al. ..................... 340/227 R X |
| 3,823,372 | 7/1974 | Hanson et al. ..................... 324/33 X |

*Primary Examiner*—Donald J. Yusko
*Assistant Examiner*—Daniel Myer
*Attorney, Agent, or Firm*—E. M. Whitacre; P. M. Emanuel

[57] ABSTRACT

An ion current is produced between two spatially separated electrodes by creating a corona discharge about one of these electrodes and causing ions to flow to the other electrode. Aerosols introduced into the region between the two electrodes interact with the flowing ions causing a resultant decrease in ion current. A decrease in ion current is sensed to indicate the presence of aerosols.

6 Claims, 6 Drawing Figures

HIGH VOLTAGE AEROSOL DETECTOR

This invention relates generally to apparatus for detecting the presence of aerosols in gases and particularly to aerosol detectors suitable for detecting particles evolved from a combustion.

Aerosol detectors generally may be categorized into two classifications: those which sense molecules that interrupt a light beam and those which sense the interaction of molecules with an ion current. In the operation of an optical aerosol detector, aerosol particles interrupt a light beam, changing the electrical output of an associated light detector. The output change of the light detector is sensed and an alarm signal generated. The optical aerosol detector has the main disadvantage of requiring a significant amount of aerosol particles in front of its detecting device in order to provide a usable signal. A design consideration in the construction of optical aerosol detectors is the requirement that an associated light source which forms part of the detector mechanism be shielded from ambient light. Relatively elaborate arrangements for shielding the detector mechanism from ambient light generally hamper ingress of aerosols to the detector typically resulting in relatively long delays prior to providing an output signal. Such aerosol detectors further have the problem of increased degradation in sensitivity as dust particles and other aerosols cover the detecting mechanism.

The second type of aerosol detector mentioned above utilizes the effect of smoke particles upon the current flow in an ionization chamber. In such devices, two electrodes are arranged in the path of the aerosol. A source of electrical potential is applied across the two electrodes. Thereafter, ion pairs are introduced in the region between the electrodes, producing a current flow in an associated external circuit. The introduction of aerosols into the region between the two electrodes causes a decrease in the mobility of the ions which causes a decrease in the current flow in the external circuit. This decrease in current flow is thereafter utilized to activate additional alarm circuitry.

The prior art is replete with ionization devices, such as the one mentioned above. These ionization devices, although varied in geometry, generally have at least one source of radioactive material for providing ion pairs in the region of the electrodes. Radioactive materials, when utilized with aerosol detectors such as those found in the prior art, have the disadvantage of being a potential health hazard in that alpha particles are generally radiated and, in addition, have the disadvantage of providing a relatively small amount of ionization in the region between the electrodes. As a result of the relatively small amount of ionization, the current in the external circuit is extremely small, requiring relatively elaborate signal amplification apparatus to achieve a desirable sensitivity. Shielding is generally necessary to decrease noise effects caused by external radiation upon the relatively sensitive signal detecting circuitry. Furthermore, periodic recalibration of both the optical aerosol detector and the radioactive source ionization type of aerosol detector is frequently required.

It is therefore desirable to provide an aerosol detector which has a relatively large output current along with a high degree of sensitivity and, furthermore, which is free of the health hazards that might be associated with a radioactive source. It is further desirable to provide an aerosol detector which will be relatively free of periodic calibration requirements.

An aerosol detector which provides these and other desirable features in accordance with the present invention is comprised of a discharge means having an electrode about which a corona discharge is developed when coupled to a source of given electric potential. A receiving means is arranged for receiving the charged particles provided by the discharge means and a current sensing means, which is coupled to the receiving means, detects a resultant current flow. Both the discharge means and the receiving means are arranged in a gas in which aerosols may be present.

A better understanding of the invention will be derived from the following detailed description and the accompanying drawings of which:

Figure 1:
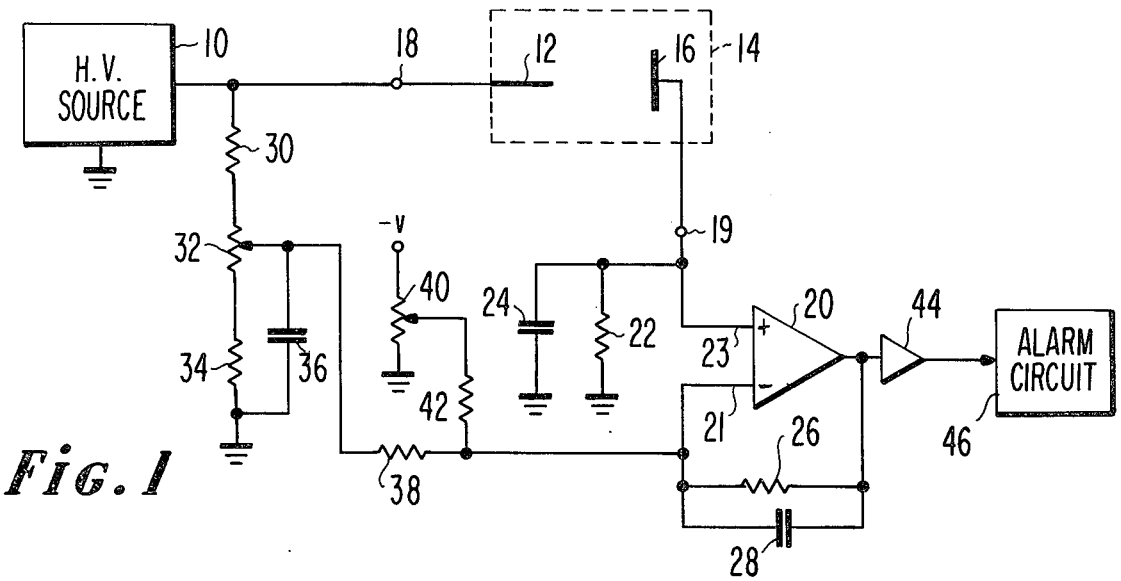
FIG. 1 is a schematic representation of a two-element aerosol detector and associated electronic circuitry in accordance with the present invention.
Figures 1A, 2:
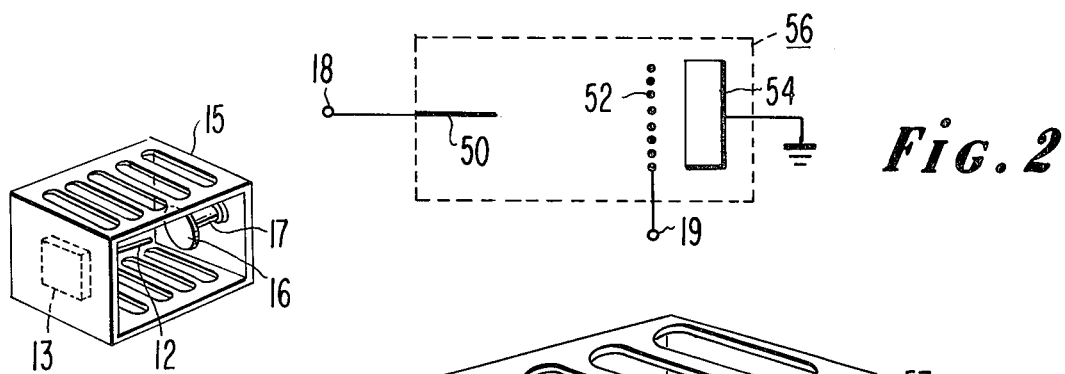
FIG. 1a is a perspective drawing of a two-element aerosol detector.
FIG. 2 is a schematic representation of a three-element aerosol detector suitable for use with the circuitry of FIG. 1.

In the apparatus of FIGS. 1 and 1a, a source of high voltage 10 is coupled through a terminal 18 to a probe 12. Probe 12 operates in conjunction with a receiving electrode 16 to form an aerosol detector 14. Illustratively, probe 12 is formed in a rod-like shape with a substantially blunt end portion that is free of sharp points or edges. A hemispherically shaped blunt end is particularly well suited for this application. Probe 12 is desirably comprised of material having a relatively high thermal conductivity such as tungsten, gold, copper, etc.

The receiving electrode 16 may be of a disc-shape having a relatively large diameter with respect to the diameter of the blunt end of probe 12. In FIG. 1a, probe 12 is illustratively mounted by an insulating block 13 to a wall of a perforated housing 15. A disc-shaped receiving electrode is mounted by a rod 17 to a wall of housing 15 opposite probe 12. Other configurations or shapes of receiving electrode 16 may operate suitably well, for example, a hemisphere, paraboloid, rectangular plate, etc. The blunt end portion of probe 12 is desirably positioned a predetermined distance from electrode 16 along an axial line passing through the center of this electrode. The diameter of the blunt end of probe 12 is chosen such that its radius of curvature is small in comparison with the radius of curvature of electrode 16 when such radius of curvature is measured along a line passing through the major axis of the probe and the center of this electrode. By properly selecting the respective radii of curvature of probe 12 and receiving electrode 16 and the spacing of these electrodes, a corona discharge may be formed about the blunt end of the probe. Spacing between probe 12 and receiving electrode 16 is such that the receiving electrode is out of the corona discharge region and in a space charge limited current region.

Electrode 16 is coupled through a terminal 19 to circuitry suitable for sensing a change in current and responsively providing an alarm signal. One example of a circuit that provides these and other desirable features is illustrated in FIG. 1. In this circuitry, terminal 19 is coupled to an amplifier 20, a resistor 22 and a capacitor 24. Resistor 22 is selected, in accordance with the current flow between probe 12 and electrode 16, such that the voltage thereacross is of the order of several volts, for example, 1 to 4 volts. Capacitor 24, coupled across resistor 22, operates as a filter to smooth the voltage across this resistor. Amplifier 20 is an operational amplifier arranged to sense the current flowing between probe 12 and electrode 16. A feedback resistor 26 is coupled between the output of amplifier 20 and an inverting input terminal 21 and is utilized to adjust the gain of amplifier 20. An integrating capacitor 28, coupled across resistor 26, operates to integrate current changes provided from aerosol detector 14. A compensating circuit is also coupled to inverting input 21 of amplifier 20 for decreasing the effect on the detector output of changes in the voltage provided by high voltage source 10. The compensating circuit includes a voltage divider comprised of the series combination of resistors 30 and 34 and potentiometer 32 coupled across the output of high voltage source 10. An output from this voltage divider is provided at the adjustable terminal of potentiometer 32 to which a capacitor 36 and resistor 38 are coupled. Capacitor 36 operates to reduce ripple in the voltage provided at the output of this voltage divider, and resistor 38 couples this output voltage to inverting input terminal 21 of amplifier 20. A further voltage divider comprised of potentiometer 40 and resistor 42 is coupled to terminal 21 of amplifier 20 for providing a desired offset voltage at the output of this amplifier.

Signals appearing at the output of amplifier 20 are coupled to a buffer amplifier 44. The purpose of amplifier 44 is to provide sufficient signal gain to drive an alarm circuit 46. Alarm circuit 46 may comprise an electronic or electromechanical sounding device, such as a bell or electronic tone alarm and may further incorporate circuitry for disabling other electrical apparatus or operating a fire extinguisher.

In the operation of the above-described circuitry, the high voltage source 10 is set at a voltage sufficient to provide a corona discharge at the blunt end of probe 12. Ions provided by the corona discharge flow within the region between the blunt end of probe 12 and the receiving electrode 16 creating a current flow in the associated external circuitry coupled to terminals 18 and 19. The current flow created in the external circuitry is of a relatively large magnitude of the order of 1 microampere. This relatively high current which is caused by the correspondingly large quantity of ions produced by the corona discharge allows circuitry to be used with this aerosol detector which is substantially free of electrical shielding requirements.

The spatial region in which the ions flow may be categorized into specific regions, a corona discharge region adjacent the blunt end of probe 12 and a space charge limited current region or passive zone between the latter region and the receiving electrode. Ions in the passive zone move at a relatively slow velocity towards receiving electrode 16 creating an ion current flow in this zone. The direction of ion current flow in the passive zone is determined by the polarity of the voltage applied to probe 12 and electrode 16. For purposes of explaining the operation of this aerosol detector, it may be assumed that a positive potential is applied to probe 12 and a negative potential applied to electrode 16.

The relatively large molecules comprising the aerosols introduced into the region between probe 12 and receiving electrode 16 appear to adhere to the flowing ions in the passive zone decreasing their mobility. This decrease in ion mobility results in a corresponding decrease of the current flow in the associated external circuitry. Amplifier 20 senses this decrease in current flow and provides a corresponding change in output voltage. The relatively high degree of sensitivity of this smoke detector to small quantities of aerosols appears to be due to some combination of the relatively large quantity and low velocity of ions in the passive zone. In the event that the aerosol flowing between the probe and receiving electrode occurs in relatively small, intermittent quantities rather than a continuous flow, the integrating effect of amplifier 20 allows a smooth output signal to be developed at the output of this amplifier rather than a series of output signals corresponding to the peak aerosol quantities between the probe and receiving electrode. Hence, a relatively steady output signal may be derived from amplifier 20 in the presence of a plurality of small quantities of aerosols making it easier to discern the presence of an aerosol from, for example, noise transients. In some applications, however, it may be desirable to detect small, intermittent aerosol quantities. In such cases, the integrating capacitor may be eliminated and the alarm circuitry adjusted to respond to signals of relatively short duration.

In some particular applications of the above-described circuitry, the high voltage source 10 may be relatively unstable. If the high voltage from source 10 varies, the ion current in the passive zone will change proportionately causing a correspondingly changed current to flow into terminal 23 of amplifier 20. Unless compensation is made to amplifier 20 for such changes in high voltage, false alarms may be created in response to decreases in high voltage. To minimize the effect of high voltage fluctuation, a compensating network is utilized. The compensating network operates in the following manner. The voltage level provided at the output of high voltage source 10 is sampled at potentiometer 32 and fed into an inverting input of amplifier 20. By providing a current into the inverting input of amplifier 20 that is proportional to the high voltage level, amplifier 20 may be made to have an output that is substantially unrelated to changes in voltage output from source 10. If output signals from amplifier 20 are made to be substantially unrelated to fluctuations in output voltage from source 10, then the changes in output voltage from amplifier 20 can be attributed substantially only to changes in aerosol quantities in the passive zone adjacent to receiving electrode 16. Voltage changes at the output of amplifier 20 may be coupled through a buffer amplifier 44 to an alarm circuit 46. Alarm circuit 46 may be arranged to operate in response to a predetermined voltage level provided at the output of amplifier 20.

The aerosol detector 14, as described above, is relatively sensitive to the presence of aerosols; however, small and infrequent amounts of aerosols in the passive zone adjacent electrode 16 may create signals at the output of amplifier 20 which are relatively brief in duration and indistinguishable from noise transients. An improved version of the above-described aerosol detector that is effective in aiding distinction between small quantities of aerosols and transient signals is illustrated in FIGS. 2 and 3 and described in detail in U.S. Pat. No. 3,932,851, entitled "Aerosol Detector" by Martin Rayl and Harold Duane Hanson, filed on even date herewith and assigned to the same assignee as the present invention. In accordance with this improved embodiment, a probe 50 is arranged in line with a screen 52 and a plate or cup member 54. This particular aerosol detector configuration may be coupled to the circuitry illustrated in FIG. 1 by substituting this apparatus at respective terminals 18 and 19. The apparatus of FIGS. 2 and 3 has the particular advantage of entrapping aerosols in the region between screen 52 and plate 54. Entrapment of aerosols in this region causes the aerosols to interact for a relatively long duration with the charged particles in the adjacent passive zone. A long interaction of aerosols with charged particles in the passive zone of the aerosol detector results in a correspondingly lengthy output signal from amplifier 20. Hence, relatively small amounts of aerosols in the passive zone of the aerosol detector 56 cause a correspondingly lengthy output signal which may be more easily distinguished from signal transients than could a signal generated, for example, from aerosol detector 14. As a result, relatively small quantities of aersols may be reliably detected.

Figures 4, 5:
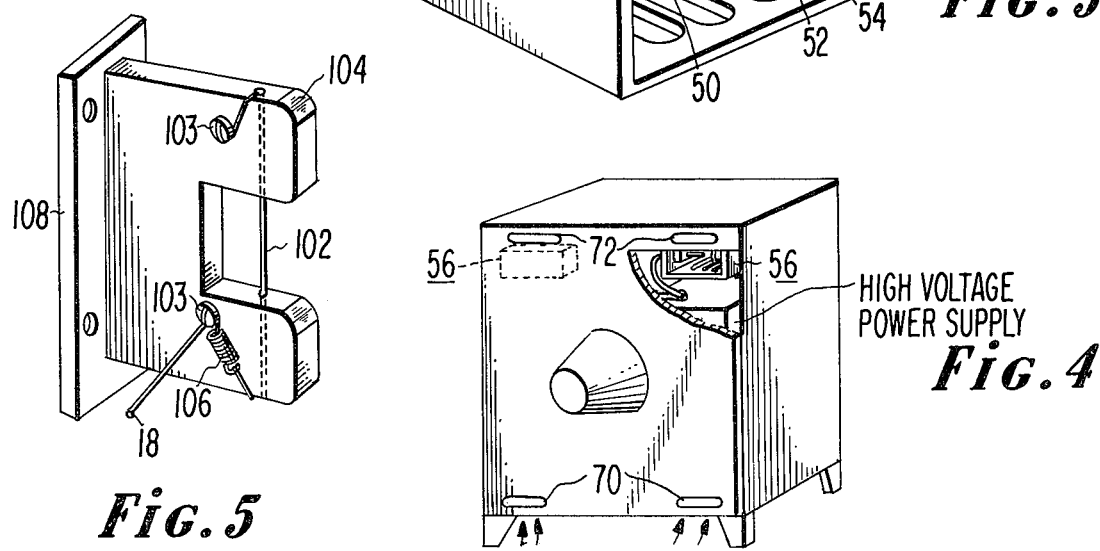
FIG. 4 is an arrangement of the apparatus of FIG. 3 in a television receiver.
FIG. 5 illustrates an apparatus suitable for providing a line corona discharge in an aerosol detector.

In a further arrangement of aerosol detectors 14 and 56, the apparatus of FIG. 5 is substituted for respective probe members 12 and 50. FIG. 5 illustrates apparatus for producing a line corona discharge and is comprised of a wire 102 fastened to screws 103 on a C-shaped insulating bracket 104. Wire 102 is maintained straight and taut, by a spring member 106 coupled in series with it. A mounting bracket 108 fastened to bracket 104 may be utilized to fasten this apparatus in an aerosol detector in place of, for example, insulating block 58 (see FIG. 3). When the apparatus of FIG. 5 is substituted for either probe 12 or 50 and an appropriate potential applied to terminal 18, a corona discharge may be produced along a portion of wire 102. The corona discharge produced by this means is effective in providing ions for an aerosol detector.

Figure 3:
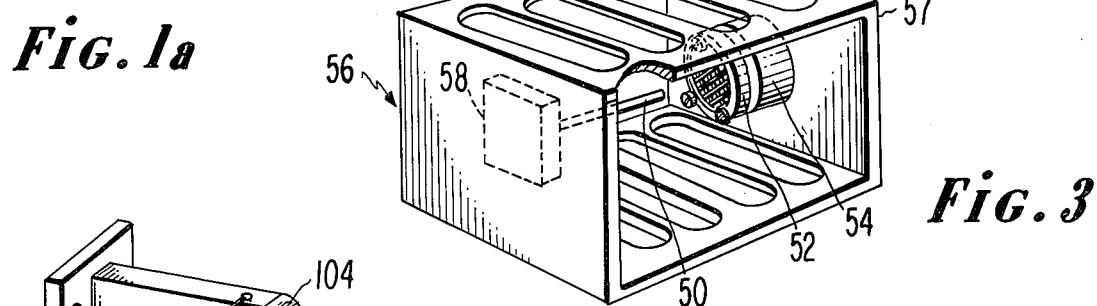
FIG. 3 is a cutaway view of the apparatus of FIG. 2.

In one particular embodiment of the apparatus illustrated in FIG. 3, an aerosol detector 56 is mounted within a television receiver as shown in FIG. 4. This arrangement is particularly advantageous for detecting smoke caused by smoldering components within a television receiver and may be utilized with circuitry, not shown, for disabling the television receiver in the event such smoke occurs. It should be noted that a television receiver utilizes a high voltage power supply for providing an accelerating potential to an electron beam in an associated image display device. This high voltage power supply generally provides adequate voltage for operating the above-described aerosol detector and may be coupled, for example, to the probe of this detector through a voltage divider at the output of the high voltage power supply or to a tap on the associated high voltage transformer. If the high voltage power supply in the television receiver is utilized with the aerosol detector, the circuitry illustrated in FIG. 1 may be advantageously employed to compensate for changes in high voltage when, for example, the brightness of the displayed image is changed.

Television receivers are generally designed so that air for cooling the associated components enters through vents 70 provided near the bottom of the receiver and exits through further vents 72 provided near the top of the receiver. By placing one or more aerosol detectors near the top area of the receiver in the path of exiting air, as shown in FIG. 4, smoke provided by any of the smoldering components can be caused to flow past the smoke detector. Furthermore, smoke and other aerosols developed outside the television receiver from, for example, a cigar or pipe, will generally not cause the aerosol detector to falsely sound an alarm. This is because such smoke tends to rise away from the television receiver's air inlets and is repelled at the air outlets. It is thus unlikely to enter into the receiver's cabinet. This feature allows the aerosol detector to be adjusted to a particularly high level of sensitivity for television receiver smoke sensing applications, since it will generally be unaffected by external sources of aerosols.

In one specific and nonlimiting example of the aerosol detector of FIG. 1, the probe member 16 was made of solid gold material having a length of about 1 inch, a diameter of about 0.025 of an inch and a hemispherical blunt end. The receiving electrode 16 was made in the shape of a disc with about a 1 inch diameter. Brass material was utilized for this electrode. The tip of the probe 12 was spaced from receiving electrode 16 by about seven-eighths of an inch. The high voltage source 10 was set at about 7500 volts with the positive terminal coupled to the probe. It was determined through experimentation that the particular geometry mentioned above provided good stability and high immunity to changes in temperature and humidity. Similarly, the apparatus of FIG. 2 was constructed utilizing the same probe material as that mentioned above with respect to probe 12. A block of Teflon material 58 was utilized to support probe 50. Screen 52 was made about one inch in diameter and spaced from a cylindrical cup shaped member 54 by about one thirty-second of an inch. Nylon screws and ceramic washers were utilized to support the screen from the cup. Cup member 54 was made of brass cylindrical material having a closed end away from the screen, an outside diameter of about one inch, an inside diameter of about seven-eighths of an inch and an internal depth of about three-eighths of an inch. An outside housing 57 supporting the aerosol detector was constructed of bakelite material.

What is claimed is:

1. Apparatus for detecting smoke in a cabinet enclosed television receiver having a high voltage power supply for providing an accelerating potential to an electron beam in an associated image display device comprising:
    means for providing a continuous corona discharge coupled to said high voltage power supply;
    a receiving means spaced a predetermined distance from said discharge means for receiving charged particles provided by said corona discharge;
    a perforated housing for enclosing said discharge means and said receiving means, arranged within said television enclosure; and
    sensing means coupled to said receiving means for providing an alarm signal in response to a predetermined decrease in current flow between said discharge means and said receiving means.

2. Apparatus according to claim 1 wherein:
    said sensing means includes an amplifier having a first input terminal for receiving current from said receiving means, a second input terminal coupled to said high voltage power supply for compensating the output level of said amplifier in response to changes in the voltage level provided to said discharge means and an output terminal for providing signals in response to current provided by said receiving means.

3. Apparatus according to claim 2 wherein:
said cabinet enclosing said television receiver includes vents for allowing ingress of air and further vents for allowing egress of said air; and
said perforated housing is mounted in close proximity to said further vents for allowing exiting air to pass therethrough.

4. Apparatus according to claim 1 wherein: said discharge means comprises a metallic cylindrical probe having a blunt end substantially free of sharp points and edges.

5. Apparatus according to claim 4 wherein: said blunt end is substantially hemispherical.

6. Apparatus according to claim 4 wherein: said receiving means comprises a disc-shaped metallic plate arranged a predetermined distance from said discharge means.

* * * * *